US00PP19112P2

(12) United States Plant Patent
Bergman

(10) Patent No.: US PP19,112 P2
(45) Date of Patent: Aug. 19, 2008

(54) ***CHRYSANTHEMUM* PLANT NAMED 'PINK YOIRVINE'**

(50) Latin Name: *Chrysanthemum×morifolium*
Varietal Denomination: Pink Yoirvine

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/705,881

(22) Filed: Feb. 14, 2007

(51) Int. Cl.
*A01H 5/00* (2006.01)

(52) U.S. Cl. ..... Plt./297

(58) Field of Classification Search ..... Plt./297, Plt./286

See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinctive cultivar of *Chrysanthemum* plant named 'Pink Yoirvine', characterized by its upright and uniformly mounded plant habit; freely branching and vigorous growth habit; dark green-colored foliage; uniform flowering response; early flowering habit, eight-week response time; freely flowering habit; daisy-type inflorescences with dark pink-colored ray florets; and good postproduction longevity.

1 Drawing Sheet

Botanical designation: *Chrysanthemum×morifolium.*
Cultivar denomination: 'Pink Yoirvine'.

CROSS-REFERENCED TO RELATED APPLICATIONS

*Chrysanthemum* Plant Named Red Yoirvine (U.S. Plant application Ser. No. 11/705,882); Wendy R. Bergman, applicant; filed concurrently.

*Chrysanthemum* Plant Named Yellow Yoirvine (U.S. Plant application Ser. No. 11/705,883); Wendy R. Bergman, applicant filed concurrently.

BACKGROUND OF THE INVENTION

The present invention relates to a new and distinct cultivar of *Chrysanthemum* plant, botanically known as *Chrysanthemum×morifolium,* commercially grown as a potted *Chrysanthemum* and hereinafter referred to by the name 'Pink Yoirvine'.

The new *Chrysanthemum* is a naturally-occurring whole plant mutation of the *Chrysanthemum×morifolium* cultivar Yoirvine, not patented. The new *Chrysanthemum* was discovered and selected by the Inventor as a single flowering plant within a population of plants of the cultivar Yoirvine in March, 2004, in Fort Myers, Fla. The selection of this plant was based on its uniform plant growth habit, vigor, freely branching habit, desirable inflorescence form and floret colors, fast response time and excellent postproduction longevity.

Asexual reproduction of the new *Chrysanthemum* by vegetative tip cuttings was first conducted in Fort Myers, Fla. in June, 2004. Asexually reproduction by cuttings has shown that the unique features of this new *Chrysanthemum* are stable and reproduced true to type in successive generations.

SUMMARY OF THE INVENTION

Plants of the cultivar Pink Yoirvine have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pink Yoirvine'. These characteristics in combination distinguish 'Pink Yoirvine' as a new and distinct potted *Chrysanthemum* cultivar:

1. Upright and uniformly mounded plant habit.
2. Freely branching and vigorous growth habit.
3. Dark green-colored foliage.
4. Uniform flowering response.
5. Typically grown as a center-budded or natural spray type.
6. Early flowering habit, eight-week response time.
7. Freely flowering habit.
8. Daisy-type inflorescences with dark pink-colored ray florets.
9. Good postproduction longevity with plants maintaining good substance and color for about four weeks in an interior environment.

Plants of the new *Chrysanthemum* differ from plants of the parent, the cultivar Yoirvine, in the following characteristics:

1. Plants of the new *Chrysanthemum* flower a few days later than plants of the cultivar Yoirvine.
2. Plants of the new *Chrysanthemum* and the cultivar Yoirvine differ in ray floret color as plants of the cultivar Yoirvine have light purple-colored ray florets.

Plants of the new *Chrysanthemum* differ from plants of the cultivars Red Yoirvine and Yellow Yoirvine primarily in ray floret color.

Plants of the new *Chrysanthemum* can be compared to plants of the *Chrysanthemum* cultivar Yoroanoke, disclosed in U.S. Plant Pat. No. 12,906. In side-by-side comparisons conducted in Fort Myers, Fla., plants of the new *Chrysanthemum* differed from plants of the cultivar Yoroanoke in the following characteristics:

1. Plants of the new *Chrysanthemum* had larger inflorescences than plants of the cultivar Yoroanoke.
2. Inflorescences of plants of the new *Chrysanthemum* and the cultivar Yoroanoke differed in ray floret color as plants of the cultivar Yoroanoke had lighter pink-colored ray florets.
3. Plants of the new *Chrysanthemum* tolerated low production temperatures better than plants of the cultivar Yoroanoke.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of typical flowering plants of 'Pink Yoirvine'.

The photograph at the top of the sheet is a close-up view of typical inflorescences of 'Pink Yoirvine'.

DETAILED BOTANICAL DESCRIPTION

The aforementioned photographs and following observations and measurements describe plants grown in Leamington, Ontario, Canada during the autumn in a glass-covered greenhouse and under conditions and practices which approximate those generally used in commercial potted *Chrysanthemum* production. During the production of the plants, day temperatures ranged from about 21° C. to 27° C., night temperatures ranged from about 17° C. to 19° C. and light levels ranged from 4,000 to 6,000 foot candles. Four unrooted cuttings were directly stuck in 15 cm. containers, exposed to long day/short night conditions, and pinched about three weeks later. At that time, the photoinductive short day/long night treatments were started. Plants used in the photographs and for the description were center-budded and were about eleven weeks old. In the following description, color references are made to The Royal Horticultural Society Colour Chart, 1995 Edition, except where general terms of ordinary dictionary significance are used. Observations and measurements were taken from a single plants.

Botanical classification: *Chrysanthemum×morifolium* cultivar Pink Yoirvine.

Parentage: Naturally-occurring whole plant mutation of the *Chrysanthemum×morifolium* cultivar Yoirvine, not patented.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Fine to thick, fibrous; white in color.

*Rooting habit.*—Freely branching; moderately dense.

Plant description:

*Appearance.*—Herbaceous daisy-type potted *Chrysanthemum* typically grown as a center-budded or as a natural spray type. Stems upright and outwardly spreading giving a uniformly mounded appearance to the plant. Freely branching habit, about four or five lateral branches develop after removal of terminal apex (pinching); dense and full plant habit. Strong and vigorous growth habit.

*Plant height.*—About 27 cm.

*Plant width.*—About 24.5 cm.

*Lateral branches.*—Length: About 23 cm. Diameter: About 4 mm. Internode length: About 2.2 cm. Strength: Strong. Texture: Pubescent. Color: 148B.

Foliage description:

*Arrangement.*—Alternate, simple.

*Length.*—About 6 cm.

*Width.*—About 4.3 cm.

*Shape.*—Palmately lobed.

*Apex.*—Cuspidate.

*Base.*—Attenuate.

*Margin.*—Palmately lobed, sinuses between lateral lobes mostly parallel.

*Texture, upper and lower surfaces.*—Fine pubescence; veins prominent on lower surface.

*Color.*—Developing and fully expanded foliage, upper surface: 147A; venation, 147B. Developing and fully expanded foliage; lower surface: 147B; venation, 147B.

*Petiole.*—Length: About 1.8 cm. Diameter: About 3 mm. Texture, upper and lower surfaces: Pubescent. Color, upper surface: Close to 147C. Color, lower surface: Close to 147B.

Inflorescence description:

*Appearance.*—Daisy-type inflorescence form with ligulate-shaped ray florets. Inflorescences borne on terminals above foliage. Disk and ray florets arranged acropetally on a capitulum. Inflorescence faintly fragrant, typical of *Chrysanthemum*. Typically grown as a center-budded or a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Freely flowering, about 20 inflorescences develop per plant.

*Inflorescence bud.*—Height: About 2.1 cm. Diameter: About 1.4 cm. Shape: Ovoid to oblate. Color: Close to 78C.

*Inflorescence size.*—Diameter: About 7.7 cm. Depth (height): About 1.8 cm. Diameter of disc: About 1.7 cm. Receptacle height: About 8 mm. Receptacle diameter: About 1.8 cm. Receptacle color: 147B.

*Ray florets.*—Shape: Ligulate. Orientation: Initially upright, then about 90° from vertical or perpendicular to peduncle; eventually reflexed. Aspect: Initially incurved, then mostly flat. Length: About 3.7 cm. Width: About 8 mm. Apex: Emarginate. Base: Attenuate; short and corolla tube. Margin: Entire. Texture, upper and lower surfaces: Smooth, glabrous; velvety. Number of ray florets per inflorescence: About 28 arranged in about two whorls. Color: When opening, upper surface: Close to 78B. When opening, lower surface: Close to 78D. Fully opened, upper surface: Close to 78A. Fully opened, lower surface: Close to 75C.

*Disc florets.*—Arrangement: Massed at center of receptacle. Shape: Tubular, elongated. Apex: Five-pointed. Length: About 7 mm. Width: About 2 mm. Number of disc florets per inflorescence: About 215. Color, Immature: Apex: Close to 5A. Mid-section: Close to 5C. Base: Close to 4D. Color, mature: Apex: Close to 7A. Mid-section: Close to 7C. Base: Close to 3C.

*Phyllaries.*—Number of phyllaries per inflorescence: About 24 arranged in about two or three whorls. Length: About 6 mm. Width: About 3 mm. Shape: Elliptical. Apex: Acute. Base: Truncate. Margin: Entire. Texture, upper surface: Smooth, waxy. Texture, lower surface: Pubescent. Color, upper and lower surfaces: Close to 148B.

*Peduncles.*—Length: First peduncle: About 5 cm. Fourth peduncle: About 8.8 cm. Diameter (first peduncle): About 1.5 mm. Angle: About 45° to 60° from vertical. Strength: Strong, flexible. Texture: Pubescent. Color: Close to 148B.

*Reproductive organs.*—Androecium: Present on disc florets only. Filament length: About 2 mm. Filament color: Close to 1C. Anther shape: Narrowly oblong. Anther length: About 2 mm. Anther color: Close to 7A. Pollen amount: Scarce. Pollen color: Close to 14B. Gynoecium: Present on both ray and disc florets. Pistil length: About 7 mm. Stigma shape: Bi-parted. Stigma color: Close to 5A. Style length: About 4 mm. Style color: Close to 4B. Ovary color: Close to 155A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 5° C. and high temperatures of about 38° C.

It is claimed:

1. A new and distinct *Chrysanthemum* plant named 'Pink Yoirvine' as illustrated and described.

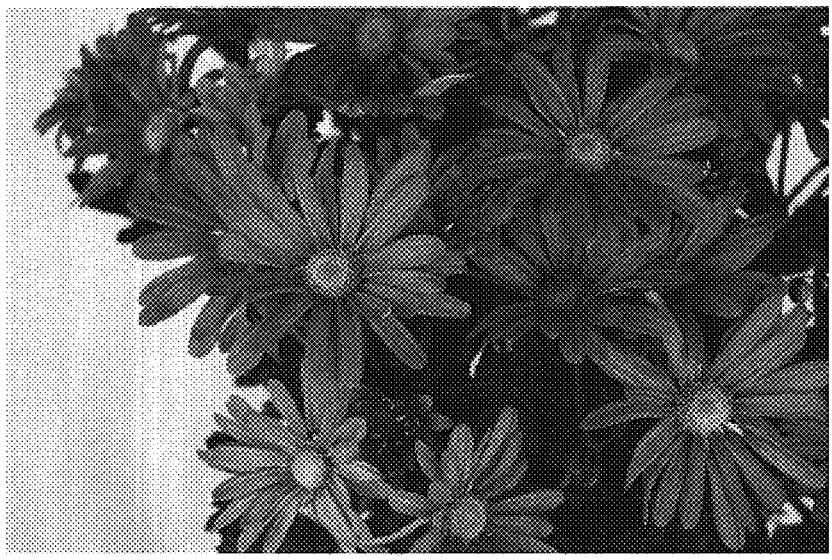
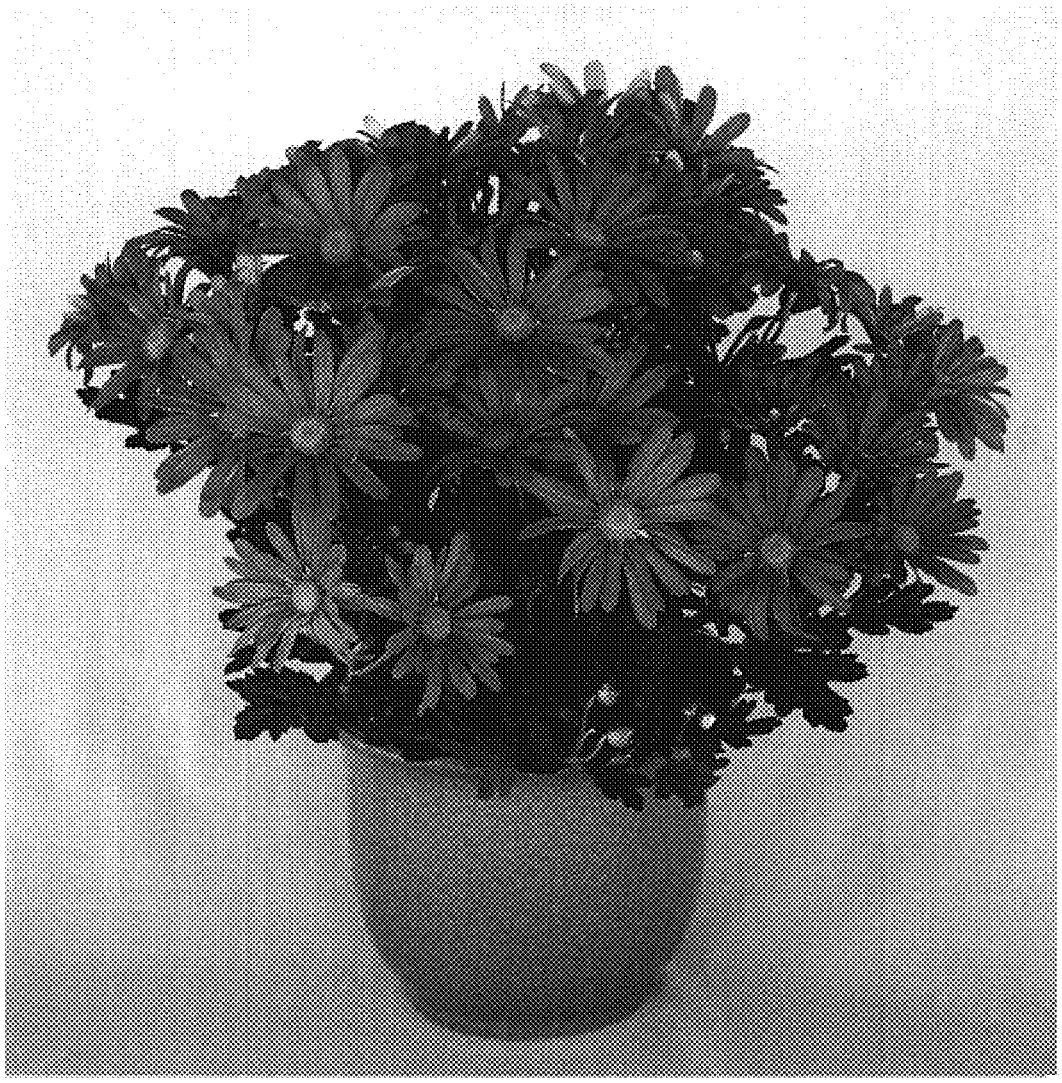

* * * * *